United States Patent
Ringwala et al.

(10) Patent No.: US 11,723,784 B2
(45) Date of Patent: Aug. 15, 2023

(54) STENT DELIVERY SYSTEM AND METHOD

(71) Applicant: MicroVention, Inc., Aliso Viejo, CA (US)

(72) Inventors: Hussain S. Ringwala, Villa Park, CA (US); Ronak Dholakia, Aliso Viejo, CA (US); Steve Trom, Costa Mesa, CA (US)

(73) Assignee: MicroVention, Inc., Aliso Viejo, CA (US)

( * ) Notice: Subject to any disclaimer, the term of this patent is extended or adjusted under 35 U.S.C. 154(b) by 125 days.

(21) Appl. No.: 17/096,730

(22) Filed: Nov. 12, 2020

(65) Prior Publication Data

US 2021/0137715 A1  May 13, 2021

Related U.S. Application Data

(60) Provisional application No. 62/934,410, filed on Nov. 12, 2019.

(51) Int. Cl.
*A61F 2/966* (2013.01)
*A61F 2/86* (2013.01)
*A61F 2/95* (2013.01)

(52) U.S. Cl.
CPC ............... *A61F 2/966* (2013.01); *A61F 2/86* (2013.01); *A61F 2/9517* (2020.05); *A61F 2210/0014* (2013.01)

(58) Field of Classification Search
CPC ...... A61F 2/86; A61F 2210/0014; A61F 2/90; A61F 2002/823; A61F 2250/0018; A61F 2250/0023; A61F 2250/0026; A61F 2/82
See application file for complete search history.

(56) References Cited

U.S. PATENT DOCUMENTS

| | | | | |
|---|---|---|---|---|
| 5,993,483 | A | * 11/1999 | Gianotti | A61F 2/90 623/1.22 |
| 2003/0135265 | A1 | * 7/2003 | Stinson | D04C 1/06 623/1.22 |
| 2004/0138736 | A1 | * 7/2004 | Obara | A61F 2/915 623/1.35 |
| 2006/0136031 | A1 | 6/2006 | Gallo et al. | |
| 2007/0021819 | A1 | 1/2007 | Krolik et al. | |

(Continued)

FOREIGN PATENT DOCUMENTS

| | | | |
|---|---|---|---|
| WO | WO-2010100488 A1 * | 9/2010 | ....... A61B 17/06166 |
| WO | WO 2018/112118 A1 | 6/2018 | |
| WO | WO 2019/246268 A1 | 12/2019 | |

OTHER PUBLICATIONS

WIPO, U.S. International Search Authority, International Search Report and Written Opinion dated Mar. 23. 2021 in International Patent Application No. PCT/US 2020/060268, 11 pages.

*Primary Examiner* — Timothy J Neal
*Assistant Examiner* — Andrew P. Restaino
(74) *Attorney, Agent, or Firm* — Inskeep IP Group, Inc.

(57) ABSTRACT

A stent, a stent delivery system, and a method of delivering a stent are described that allow the porosity of the stent to be changed dynamically during a delivery procedure. Unlike prior stents and procedures that are configured to deploy with a predetermined porosity, the physician can create a region of high stent porosity over certain vessel features, a low stent porosity over other vessel features, and can create these porosity changes with at least one stent or stent layer.

20 Claims, 16 Drawing Sheets

(56) References Cited

U.S. PATENT DOCUMENTS

| | | |
|---|---|---|
| 2007/0185563 A1 | 8/2007 | Zarbartany et al. |
| 2008/0161837 A1* | 7/2008 | Toso .................... A61F 2/0045 |
| | | 606/151 |
| 2008/0167707 A1 | 7/2008 | Marrey et al. |
| 2016/0199204 A1 | 7/2016 | Pung et al. |
| 2016/0228134 A1 | 8/2016 | Martin et al. |
| 2016/0375175 A1* | 12/2016 | You ........................ A61L 27/54 |
| | | 604/514 |
| 2017/0304087 A1 | 10/2017 | Berez et al. |
| 2017/0304093 A1* | 10/2017 | Düring ..................... A61F 2/90 |

* cited by examiner

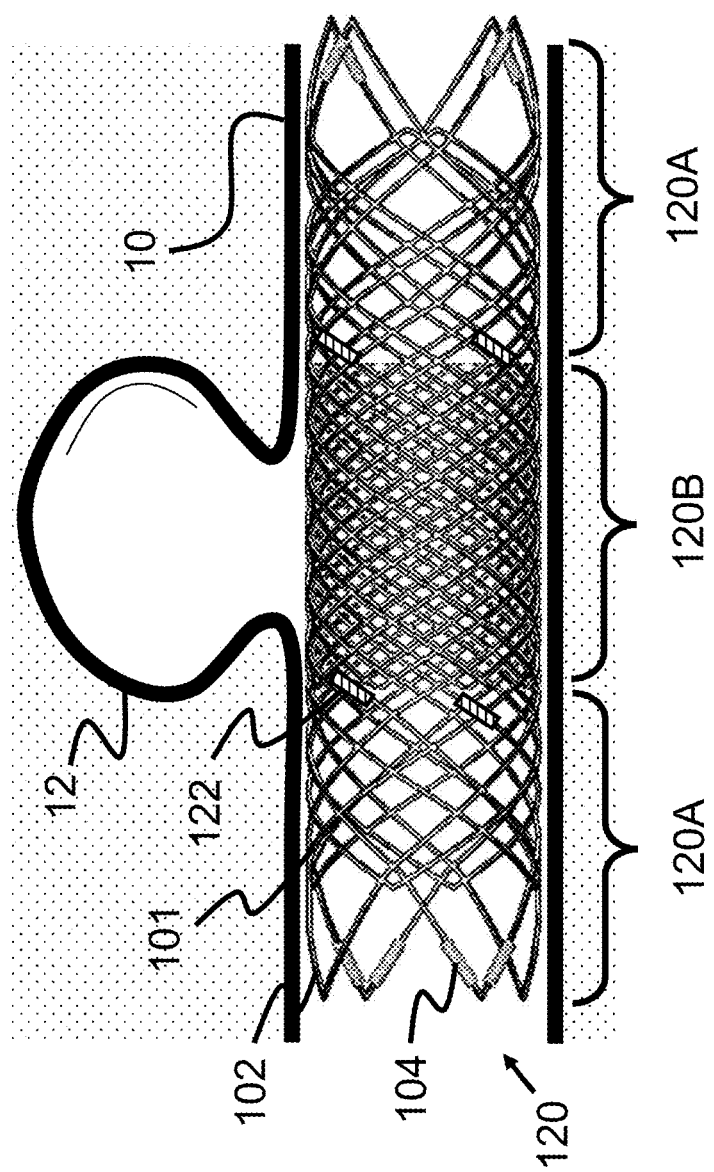

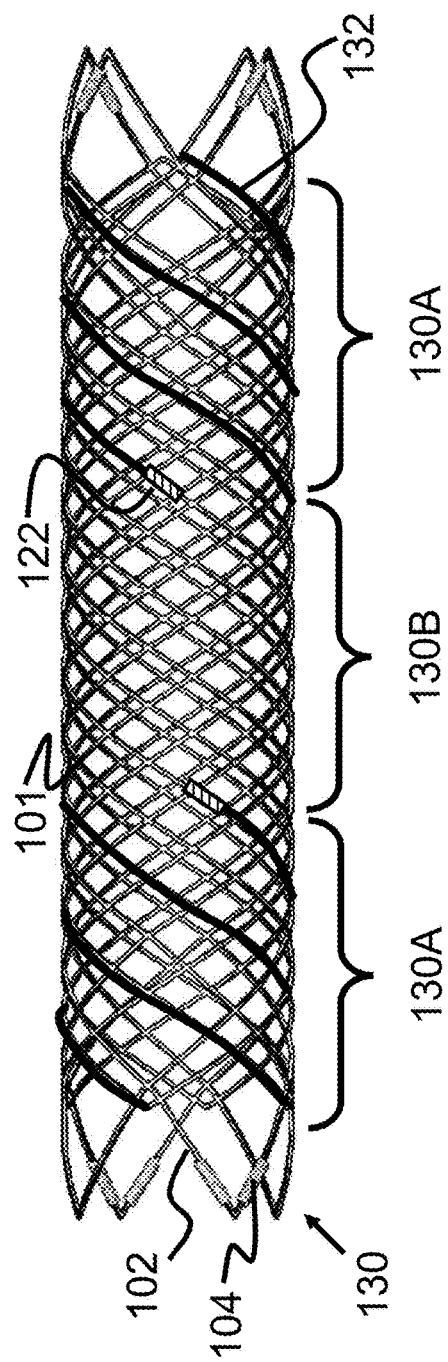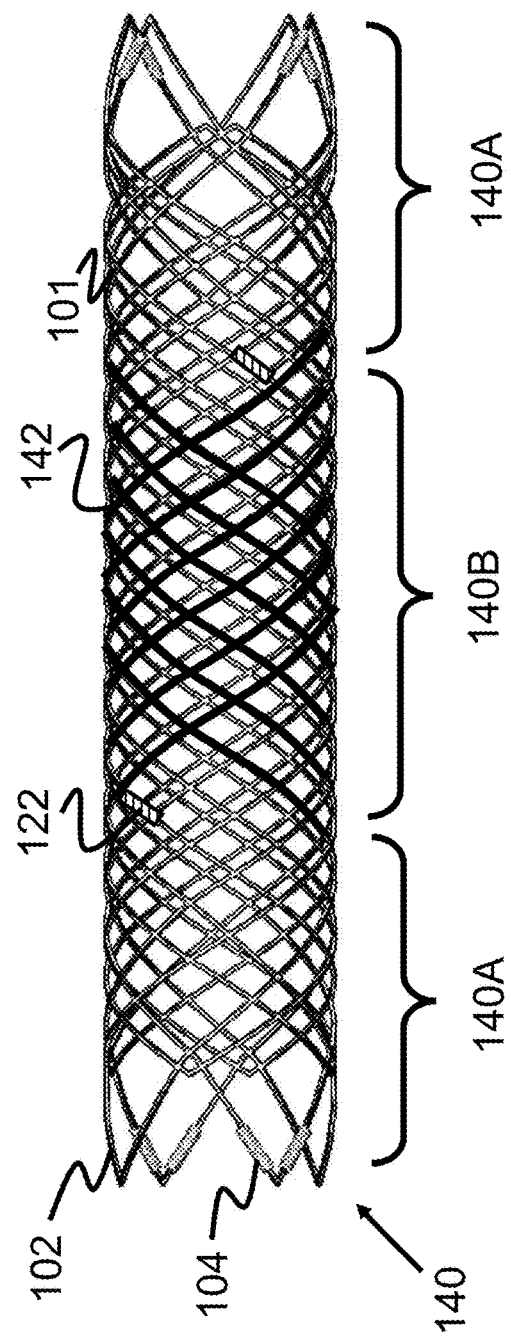
Figure 3
Figure 4

STENT DELIVERY SYSTEM AND METHOD

RELATED APPLICATIONS

This application claims priority to U.S. Provisional Application Ser. No. 62/934,410 filed Nov. 12, 2019 entitled Dynamic Stent System which is hereby incorporated herein by reference in its entirety.

BACKGROUND OF THE INVENTION

Stents are deployed within a patient's vasculature system for a variety of different treatment purposes, such as expanding narrowed portions of a vessel or covering an opening of an aneurysm or similar vascular defect. Physicians typically select a stent for treating a patient based on one or more of the stent's characteristics, such as expanded diameter, length, porosity, and ease of deployment, among others. Hence, stents are typically manufactured with different diameter, length, and porosity options to best suit a patient's treatment needs.

Porosity refers to the ratio, often expressed as a percentage, of the volume of the pores, interstices, or open areas of a stent wall. A relatively high porosity correlates with a larger amount of open space (e.g., pore openings with a larger size and/or greater frequency) while a relatively low porosity correlates to a smaller amount of open space (e.g., pore openings with a smaller size and/or reduced frequency). A desired porosity of a stent wall can be determined with one or more of many different characteristics of a stent, such as its wire diameter, its braid pattern, and the number of layers that form its stent wall.

In some treatment circumstances, it can be desirable for a stent to have a relatively high porosity, such that there are many and/or relatively large openings through the sidewall of the stent. For example, FIG. 1A illustrates an aneurysm 12 that bulges outwardly along a sidewall of a patient's vessel 10. Aneurysms 12 are sometimes treated by delivering embolic material, such as small sized coils sometimes known as microcoils, into the aneurysm 12. An intraluminal support or "coil assist" stent 100 is typically deployed across the opening of the aneurysm 12 to help contain the embolic material (either prior to or after delivery of the embolic material). Intraluminal support stents 100 are typically composed of relatively thicker wires to help anchor their position in the vessel and to allow embolic delivery catheters to pass through, if the embolic material is delivered after the stent. Hence, these stents also tend to be relatively porous (e.g., larger pore openings) in their construction and do not always prevent or significantly reduce blood from entering an aneurysm 12.

Alternatively, it may be desirable for a stent to have a relatively low porosity, such that there are few and/or relatively small opening through the sidewall of a stent. To further reduce blood flow into the aneurysm 12, the physician may deploy a second flow diverting stent (not shown in FIG. 1A) that is much less porous either within a deployed intraluminal support stent 100 or by deploying a intraluminal support stent 100 within a previously deployed flow diverting stent. In other words, the flow diverting stent can be located inside or outside of the intraluminal support stent 100. Alternately, some intraluminal support stents, such as stent 111 of FIG. 1B, may have an inner flow diverting layer 113 already attached, such as shown in U.S. Pat. No. 9,439,791, the contents of which are hereby incorporated by reference. These types of stents are known as flow diverters and use the low porosity flow diverting layer 113 to reduce blood flow to the aneurysm 12. This is an alternative treatment procedure, not necessarily requiring the embolic coils as discussed earlier. In this way, a lower porosity flow diversion stent 111 is distinguished from a higher porosity intraluminal support stent 100.

However, depending on the anatomy of the vessels at the patient's treatment site, it may not be desirable for the physician to block blood flow immediately adjacent to the opening of an aneurysm 12. Returning to the examples of FIGS. 1A and 1B, other vessels 14 may feed into or out of vessel 10. While an intraluminal support stent 100 may have a porosity large enough to allow blood flow between the vessels 10 and 14, a less porous flow diverting stent 111 may undesirably block such a nearby vessel 14. In the case of brain aneurysms, the vessels within the brain are typically small, which can present difficulties in aligning a flow diverting stent in a manner to cover an aneurysm without covering an adjacent vessel.

Further, while stent manufacturers typically provide a range of stent sizes, a desired size and porosity of flow diverting stent may not always be readily available to the physician at the time of a procedure. In that respect, there is not always a single stent capable of meeting all of the support and blood diverting qualities a physician may desire.

Further, most stents currently on the market are configured as a single porosity across their entirety length. In this way, these uniform porosity stents are not designed to have regions of different porosities and therefore are typically capable of only one particular treatment function (e.g., either low porosity for flow diversion, or high porosity for coil-assisted stenting—but not both).

Therefore, what is needed is a stent, a stent delivery system, and/or a stent delivery method that provides a physician greater control of where a region of decreased porosity delivered within a patient and what the porosity of that region is.

SUMMARY OF THE INVENTION

The present embodiments are generally directed to a stent, a stent delivery system, and a method of delivering a stent that, either separately or in combination, adjust the porosity of the stent during delivery. During delivery, the physician can create a region of high stent porosity over certain vessel features (e.g., adjacent vessel openings), a low stent porosity over other vessel features (e.g., an aneurysm), and can create these porosity changes with at least one stent or stent layer. Hence, a physician can use a single stent for some procedures in which multiple stents were previously needed and can dynamically adjust the stent's porosity during the procedure as needed.

One embodiment includes a stent having at least a first region with a relatively high resistance to longitudinal compression and a second region with a relatively low resistance to longitudinal compression. In one example, one region configured with a relatively low resistance to longitudinal compression is softer than another region configured with a relatively high resistance to longitudinal compression. Additional high and low resistance stent regions can also be included, such that there are one or more high resistance regions and one or more low resistance regions (e.g., 1, 2, 3, 4, 5, or more regions of each).

The longitudinal compression resistance of different regions of a stent can be achieved in several different ways, such as including larger diameter wires to increase resistance, including smaller diameter wires to reduce resistance, changing a braid pattern to increase/decrease resistance, changing a material of a wire, or changing a coating or plating on a portion of a wire. These techniques can be used individually or in any combination with each other.

Another aspect of the present embodiments are directed to a method of producing longitudinal compression on a stent during delivery by pushing an elongated stent pusher and retracting an outer delivery catheter. The pushing and pulling can be performed in a manner such that there is a net increase in longitudinal compression on the stent (i.e., more pushing than pulling), which causes at least a region of the stent to longitudinally compress and therefore decrease in porosity or increase in its percent metal coverage. Depending on the ratio of the pushing and the pulling, different porosities can be achieved. This pushing and pulling can be performed simultaneously or sequentially. Additionally, this technique can be used with a stent configured with higher and lower longitudinal compression resistance or with braided stents having a generally uniform longitudinal compression resistance.

Another aspect of the present embodiments are directed to a delivery system that helps indicate or cause the push/pull movement of the pusher relative to the delivery catheter. In one example, the pusher and/or the delivery catheter can include a plurality of measuring indicia along their length to indicate their relative movement and thereby act as a guide to the physician as to how much pushing and pulling is achieved.

In another example, one or more handle devices can be used to push the stent pusher, retract the delivery catheter, or both. The one or more handle devices can be configured to provide predetermined push/pull ratios between the stent pusher and the delivery catheter.

BRIEF DESCRIPTION OF THE DRAWINGS

These and other aspects, features and advantages of which embodiments of the invention are capable of will be apparent and elucidated from the following description of embodiments of the present invention, reference being made to the accompanying drawings, in which:

FIG. 2 is a side view of a stent with a decreased porosity region, according to one embodiment.

FIG. 3 illustrates a side view of a stent having regions of different longitudinal compression strength, according to one embodiment.

FIG. 4 illustrates a side view of a stent having regions of different longitudinal compression strength, according to one embodiment.

DESCRIPTION OF EMBODIMENTS

Figure 1A:
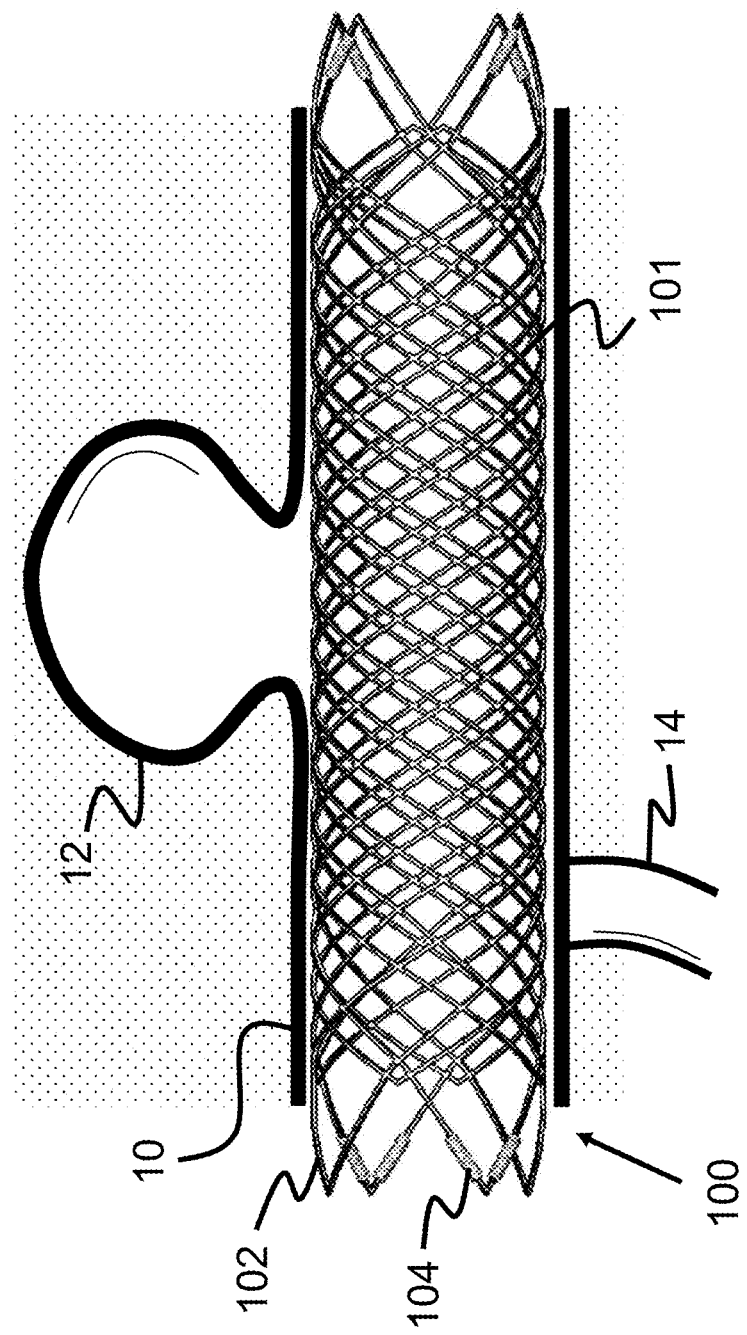
FIG. 1A is a side view of a stent positioned across an aneurysm.

Specific embodiments will now be described with reference to the accompanying drawings. These embodiments may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the embodiments. In the drawings, like numbers refer to like elements. While different embodiments are described, features of each embodiment can be used interchangeably with other described embodiments. In other words, any of the features of each of the embodiments can be mixed and matched with each other, and embodiments should not necessarily be rigidly interpreted to only include the features shown or described.

The present embodiments are generally directed to a stent, a stent delivery system, and a method of delivering a stent that, either separately or in combination, adjust the porosity of the stent during delivery. During delivery, the physician can create a region of high stent porosity over certain vessel features (e.g., adjacent vessel openings), a low stent porosity over other vessel features (e.g., an aneurysm), and can create these porosity changes with at least one stent or stent layer. Put another way, the stent, as a whole, may have a generally uniform braid angle during delivery and the physician can change this braid angle during delivery in certain regions to adjust the porosity. Hence, a physician can use a single stent for some procedures in which multiple stents were previously needed and can dynamically adjust the stent's porosity during the procedure as needed. Braid angle is discussed in more detail later in this specification.

While the present embodiments are generally described in connection with treating aneurysms (e.g., used for flow diversion, or for stent-assisted coiling techniques), it should be understood that these stents and delivery methods can be used to treat a variety of other medical conditions, such as vessel stenosis treatment, vasospasm treatment (both of which involve treating a narrowing or constriction of the blood vessel). Therefore, while these stents and delivery methods may be particularly helpful in treating aneurysms, the present embodiments should not be limited only to such treatment.

Figure 1B:
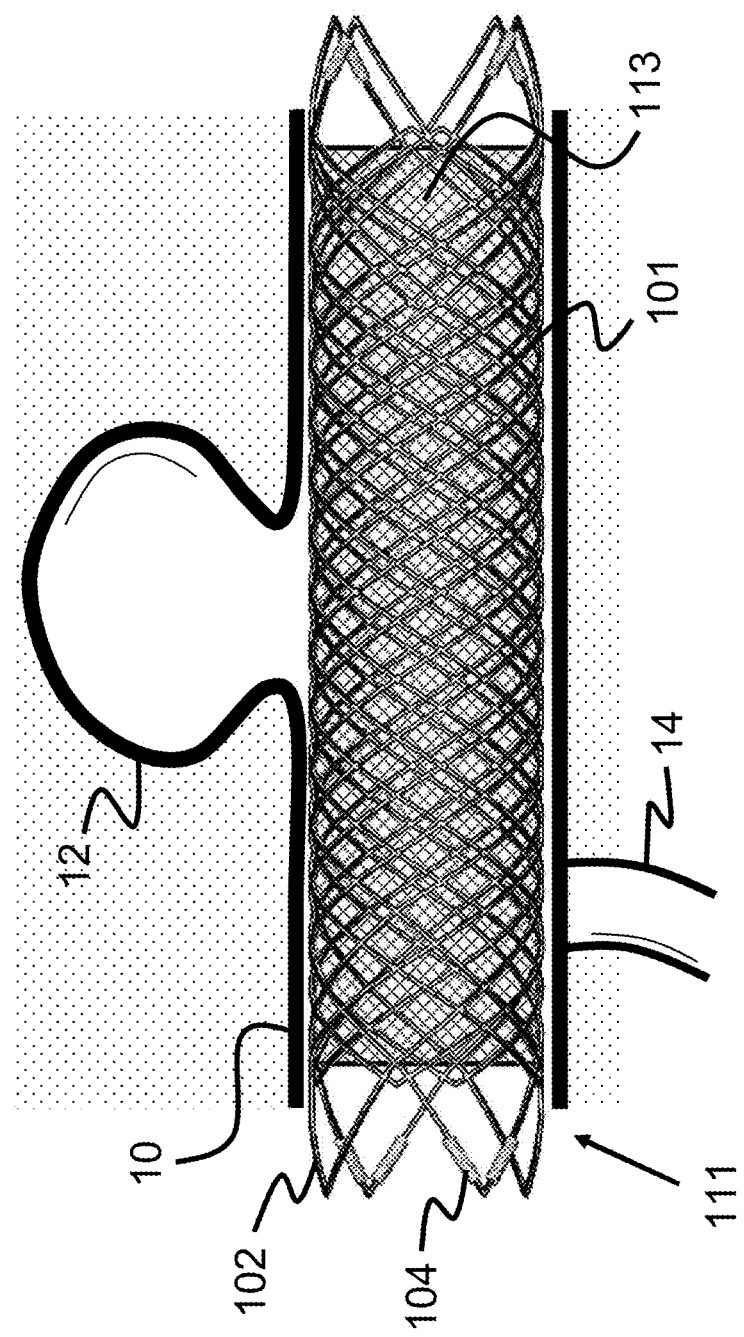
FIG. 1B is a side view of a flow diverting stent positioned across an aneurysm.

FIGS. 1A and 1B illustrate an example treatment site in which an aneurysm 12 is connected to a sidewall of a vessel 10. Aneurysms 12 are sometimes treated by delivering an intraluminal support stent 100 across the opening of the aneurysm 12 and then delivering embolic material, such as small coils sometimes called microcoils, through the stent 100 and into the aneurysm 12. Intraluminal support stents 100 are typically composed of relatively thicker wires to help anchor their position in the vessel and therefore also tend to be relatively porous (e.g., larger pore openings) in their construction.

However, depending on the anatomy of the vessels at the patient's treatment site, it may not be desirable for the physician to block blood flow immediately adjacent to the opening of an aneurysm 12. For example, another vessel 14 may feed into or out of vessel 10. While an intraluminal support stent 100 may have a porosity large enough to allow blood flow between the vessels 10 and 14, a less porous flow diverting stent may undesirably block such a nearby vessel 14, as seen in FIG. 1B.

Stents that are currently available on the market typically utilize a continuous porosity profile. In other words, they are manufactured (e.g., braided and heat set) to form a uniform porosity throughout almost their entire length when deployed in a relatively straight, uniform vessel. In this manner, the typical stent does not allow the physician to determine the porosity of sections of the stent during a procedure. For instance, if the vessel condition of FIG. 1B is being treated with a flow diversion stent 111 (e.g., where a low porosity is used to reduce blood flow into the aneurysm 12), the continuous porosity profile of the typical stent would ensure nearby vessel 14 is also covered by a low porosity region since the entire stent has a similar porosity profile. While the low porosity profile is helpful in the vicinity of the aneurysm 12 (e.g., where stent 111 is used for flow diversion), the low porosity profile is not necessarily beneficial relative to the nearby blood vessel 14 where it can cause reduced blood flow to vessel 14.

To address this problem, some embodiments presented herein utilize a stent in which sections or regions of differing porosity can be created by the physician during a treatment procedure.

FIG. 2 illustrates a stent 120 according to one embodiment that has been delivered to have regions of lower and higher porosity. Specifically, the example stent 120 includes proximal and distal end regions 120A that have a relatively high porosity compared to a relatively low porosity middle region 120B. Alternately, the relatively lower porosity region can be created in either the proximal or distal regions 120A, both regions 120A, or even throughout most or all of the entire stent 120.

As discussed in further detail below, delivery of the stent 120 with regions of different porosity can be achieved by 1) constructing the stent 120 in a manner that regions of the stent longitudinally compress a greater amount during the delivery and deployment process, 2) delivering the stent 120 through a combinations of pushing and pulling of an inner delivery pusher and an outer delivery catheter, or 3) a combination of both stent construction and delivery technique. In some embodiments, stent 120 can be delivered to have regions of different porosity, such that stent 120 initially has a first (e.g., uniform) porosity, and then forms one or more regions of different porosity upon being delivered. While stents with regions of reduced resistance to longitudinal compression may be helpful to achieve this porosity change during a procedure, stents with a generally uniform resistance to longitudinal compression may also be used.

Longitudinal compression refers to a reduction in length between a proximal and distal end of a region of a stent (left and right sides, in the figures). Resistance to longitudinal compression refers to the resistance provided in regions of stent to such longitudinal compression.

Turning first to stent construction, a stent 120 can be manufactured such that certain regions longitudinally compress more easily and other areas are relatively more resistant to compression. During deployment of the stent 120 (e.g., distal pushing), the more resistant regions to longitudinal compression will generally resist significant compression while the less resistant regions will longitudinally compress to a much greater extent, depending on how much distal, longitudinal force is applied by the physician during the delivery process.

FIG. 3 illustrates one example embodiment of a stent 130 having proximal and distal regions 130A that are more resistant to longitudinal compression and a middle region 130B that is less resistant to longitudinal compression. Specifically, the stent 130 is braided with one or more wires that are relatively more resistant to bending than the remaining braided structural wires 101.

In one example, the compression resistant regions 130A can each be woven with one or more longitudinal support wires 132 that have a larger diameter than the remaining structural stent wires 101. For example, the wires 132 may have a diameter that is within an inclusive range of 1 to 50% larger than the remaining wires 101. In another example, the wires 132 may have a diameter that are within an inclusive range of about 0.0005 to about 0.001 inch larger than the remaining wires 101. Larger diameter wires 132 will tend to be stronger than remaining smaller diameter structural stent wires 101 and thus resist compression better, and in this way regions 130A will be more compression resistant than other regions of stent 130.

In one example, the main body of the stent (e.g., an entire length of stent 130) can be woven with a single wire or a plurality of wires 101, and at least one wire 132 can also be woven amongst the one or more wires 101 in the areas intended to resist longitudinal compression (e.g., regions 130A). In this manner, one or more wires 101 are woven throughout stent 130 and one or more larger diameter wires 132 are selectively woven throughout the compression resistant regions 130A of stent 130.

Alternately, the at least one wire can be connected in a manner other than braiding. As seen in stent 144 of FIG. 5, a wire 146A can be connected longitudinally along the length of stent 130 via a plurality of loosely configured ties (not shown). The ties can allow each end of the wire 146A to slide along the wire 101 that it is attached to so that the longitudinal wire 146A does not prevent or restrain radial expansion and the foreshortening (i.e., the longitudinal shrinking of the stent that occurs as the stent radially expands) that accompanies it. In other words, the sliding ties may allow the wire 146A to slide and accommodate the foreshortening during expansion. The longitudinal wire may alternately comprise a plurality of wire segments 146B (also seen in FIG. 5) which can be aligned both linearly or nonlinearly relative to the longitudinal axis of the stent 144. Wires 146A, 146B, or a combination of the two can be used to create the regions of higher longitudinal compression resistance 144A verses the regions of lower longitudinal compression resistance 144B.

In another embodiment, previously described wires 132 can be composed of a material that is different than that of the wires 101 to provide differences in the ease of longitudinal compression. This material difference can be in addition to the previously described diameter difference or as an alternative to it. In one example, the stent wires 101 may be composed of Nitinol while the compression resistant wires 132 are composed of stainless steel, tantalum, or platinum. Additionally, material differences can be created in other ways, such as coating or electroplating a first material over a wire formed from a second material.

In another example, some or all of the wires 101 can be composed of drawn-filled tubes. Drawn-filled tubing wires can comprise a radiopaque core material (e.g., platinum or tantalum) and a shape-memory jacket or outer layer (e.g., Nitinol). One advantage of a drawn-filled tube wire stent is that the entire length of the stent has some radiopaque visibility due to the inclusion of the radiopaque material in the wire, which may reduce or eliminate the need for additional radiopaque markers to be added. Furthermore, as a drawn-filled tube stent is typically softer than a traditional stent, the medial section may even be more conformable to thereby conform to the geometry of the treatment location. In this way, drawn-filled tube stents can potentially be sized smaller and are generally less stiff than traditional stents since no separate radiopaque material is needed for visualization. Additional techniques can be used to increase the longitudinal compression resistance of some regions of a stent composed mostly of drawn-filled tubes, as discussed elsewhere in this specification. One example of a stent composed of drawn-filled tube wires can be found in U.S. application Ser. No. 16/685,995, filed Nov. 15, 2019, the contents of which are incorporated herein by reference.

Since a stent composed of drawn-filled tubing wire can provide relatively softer longitudinal compression (e.g., relative to some other metal wires such as nitinol) and the drawn-filled tubing wires can be radiopaque, it may be especially easy for a physician to view the entirety of the stent under fluoroscopic visualization or similar techniques while applying a desired amount of longitudinal compression to the stent (the compression techniques of which are discussed later in this specification). Depending on the visualization technique, the physician may be able to view the porosity of the entire stent and compress it until one or more regions of the stent achieve a desired porosity change. In other words, the physician can not only easily see what region of the stent they are applying the longitudinal compression to but can also see the relative amount of compression and porosity that is applied. In this respect, one embodiment of this specification also includes a method of visualizing a drawn-filled tubing wire stent, applying longitudinal compression, and determining when a desired change in porosity has been achieved. This determination of a desired change in porosity can be determined relatively by comparing uncompressed regions of the stent to compressed regions (e.g., through visual inspection), or by using a guide or measurement device (e.g., built in to the fluoroscope) to measure pore sizes of the stent.

In one embodiment, the structural wires 101 of the stent are a metallic (e.g., nitinol, stainless steel, or cobalt-chromium) and can comprise one or more wires wound into a single-layer tubular shape. In one embodiment, the stent is comprised of one or more drawn-filled tube wires wound into a braided, single layer tubular shape.

In another example, the different regions 130A and 130B may have different braiding patterns that increase or decrease the resistance to longitudinal compression by different amounts. For example, helical braiding, circumferential braiding, and multiple layer braiding can be used in various regions of stent 130.

As seen in FIG. 4, it is possible that most or all of the wires in a region 140A, 140B of a stent 140 can have characteristics that strengthen or weaken longitudinal compression. For example, the proximal and distal regions 140A may be braided almost entirely with wire portions that are relatively resistant to longitudinal compression while the middle region 140B may be braided almost entirely with wire portions that are relatively less resistant to longitudinal compression.

These regions 140A and 140B can be created in different ways. For example, different regions can be separately braided and then attached to each other (e.g., by welding or wire ties). Each region can be wound with one or more wires of different diameter, different material, different braiding patterns, or any combinations of these techniques.

In another example, a single wire may be formed from segments of wires having different materials or diameters. The different segments are of lengths and spaced such that segments of a certain material/size align at different regions of the stent. For example, as a wire is braided on a mandrel, a first segment of the wire aligns with segment 140A and a second segment with a different diameter/material aligns with region 140B.

In another example, the stent 140 can be first braided with one or more wires 101 and then treated to create size or material changes in each region of the stent 140. In one technique, the stent 140 can be braided with one or more structural wires 101 and the middle region 140B can be electro polished to decrease the diameter of the portions of the one or more wires 101 in that region 140B, thereby reducing resistance to longitudinal compression of regions 140B relative to adjacent regions 140A. Alternately, the stent 140 can be braided with one or more wires 101 and the proximal and distal end portions 140A can be electroplated or coated to increase the diameter of the portions of the one or more wires 101 in those regions 140A—thereby increasing the resistance to compression along regions 140A. This coating or electroplating can create a new layer of the same material on wire portion 142 as portions 101 or can coat/plate a different material on wire portion 142.

Again, the regions 130A, 130B, 140A, 140B of stent 130 can have locations different from those shown in FIGS. 3 and 4. For example, regions 130A and 1306 can be reversed. In another example, a stent may have 2, 3, 4, 5, 6, or more regions with different combinations of regions with different resistances to longitudinal compression.

Generally, the regions of reduced longitudinal resistance are configured such that they compress with an amount of force less than what would cause a deployed distal end of the stent to move or slide within a patient's vessel. Put another way, it is typically undesirable for a stent to slide within a patient's vessel once it has been partially deployed, since this may misalign the stent with its intended target site. Since distal pushing force is applied to the stent to cause longitudinal compression, it is preferable that the region of reduced longitudinal compression resistance longitudinally compresses before any anchoring force of the distal end of the stent is overcome. In some examples, a region of reduced longitudinal compression resistance is configured to longitudinally compress when an inclusive range of about 1 to 5 lbs of longitudinal force is applied to it from the pusher.

While a stent can be constructed with discrete regions of different resistance to longitudinal compression, a stent may also be created with gradual changes in longitudinal compression. For example, longitudinal compression may be the easiest (meaning the least resistance to longitudinal compression occurs) in the middle of a stent and gradually increase towards its proximal and distal ends. Such a stent can be constructed, for example, by braiding decreasing numbers of compression resistant wires 132 from the ends towards the middle of the stent. Alternately, one or more compression resistant wires 132 can have a diameter that decreases from the ends toward the middle of the stent and that is braided with wires 101 (meaning the wire 132 diameter is thickest at the ends and smallest in the middle). In another alternate example, the stent can have a braid pattern that gradually weakens its longitudinal compression resistance towards the middle of the stent.

The stents 130 and 140 (or any other stents of the present specification) can include radiopaque components to help in visualization during a procedure and that help indicate regions of different compression resistance. For example, the compression resistant wires 132 in FIG. 3 may be composed or coated with a radiopaque material. In another example, radiopaque markers or wire coils 122 can be fixed or wrapped around wires 101, 132, or 132 at locations around the circumference of the stent and at locations near an edge of a region of different compression resistance (e.g., between regions 130A and 130B). In a specific example, radiopaque markers are positioned at a proximal and distal end of a stent region having reduced longitudinal compression resistance.

The example stents of this specification are depicted as intraluminal support stents that are formed from at least a single wire 101 braided into a tubular shape with a plurality of loops 102 at each end, and with a plurality of radiopaque coils 104 on at least some of the loops 102. Such a stent is generally discussed in U.S. Pat. No. 9,439,791, the contents of which are incorporated herein by reference. Other aspects and variations of such a stent and example delivery mechanisms can be found in U.S. Pat. Nos. 10,182,931; 10,322,020; 10,335,299; 10,617,544; which are also incorporated herein by reference. However, other braided stent designs can also be used according to the present embodiments.

In some examples, a stent is classified as a flow diverter if the metal surface coverage of the device (meaning the total area of the metal comprising the stent, as a function of the total area taken up by the stent) is at least 30%. Flow diverters typically have relatively higher metal surface coverage and lower porosity since these stents are designed to reduce blood flow to an aneurysm. On the other hand, coil-assisted stents can have metal surface coverage below 30% (for example, about 20%-36%) and generally have lower metal surface coverage and higher porosity than flow diverters since the stent pores are often used as an access point for a microcatheter which is passed through one of the pores to deliver embolic material (e.g., embolic coils) in the aneurysm. In current medical practice, stents are typically classified as either intraluminal support stents or flow diverter stents (in the context of aneurysm treatment) due to their fixed porosities at given sizes and therefore these stents are each typically used for only one therapeutic purpose.

In some examples, a stent can be delivered to have at least one high porosity section that can be considered as an intraluminal support region and at least one low porosity section that can be considered as a flow diversion region. For instance, a medial portion of a stent can be delivered to have a lower porosity and be considered as a flow diversion region while the ends of the stent can have a higher porosity and be considered as an intraluminal support region.

It should be emphasized that the regions of different porosity in the stents of some embodiments are created and controlled during the delivery process to allow the physician control over where the porosity of the stent should be changed (i.e., what region of the stent) and to what amount the porosity should be changed. At least some of the stents described in this application, such as stents 100, 120, 130, and 140, can expand to a relatively uniform porosity by themselves without significant longitudinal compression and therefore this longitudinal compression remains an important mechanism for changing this initial porosity of a stent. For instance, the stents 100, 120, 130, 140 may have regions with different wires counts or wire thicknesses, but this may not have a significant impact on the porosity of the various sections by itself—instead these techniques are used to change the longitudinal compression profiles in different regions of the stent. A delivery step which is described herein longitudinally compresses one or more regions of the stent to then change the porosity profiles along different regions of the stent, during the stent delivery process.

In that respect, the present embodiments also includes one or more methods of deploying a stent to create a stent region with a different porosity. These methods can be used on standard intraluminal support stents, such as stent 100 to change porosity (i.e., stents with a relatively uniform resistance to longitudinal compression), or can be used with stents having regions of different longitudinal compression strengths, such as stents 120, 130, and 140. Further, stents with existing porosity changes (e.g., regions with higher porosity in a non-longitudinally compressed state) can also be used with the construction techniques and deployment methods described herein.

One embodiment is directed to a method of creating longitudinal compression on a stent during stent deployment. In one example embodiment, this longitudinal compression is created by advancing a pusher or elongated stent deployment mechanism distally after a portion of a stent has been deployed.

In another example embodiment, longitudinal compression is created by a combination of 1) advancing a pusher or elongated stent deployment mechanism distally after a portion of a stent has been deployed, and 2) retracting an outer delivery catheter surrounding the stent. The pusher and delivery catheter can be pushed and retracted in various ratios to achieve a desired porosity of the stent. The pushing and pulling can be performed simultaneously or in alternate increments. Generally, withdrawing the outer delivery catheter exposes portions of the stent while distally advancing the inner pusher forces a proximal portion of the stent distally forward. Since a distal end of the stent is initially expanded and anchored first within a patient's vessel, the distal end of the stent will generally remain in place, causing more proximal portions of the stent to longitudinally compress, thereby increasing the porosity in stent regions close to the delivery catheter.

Figure 5:
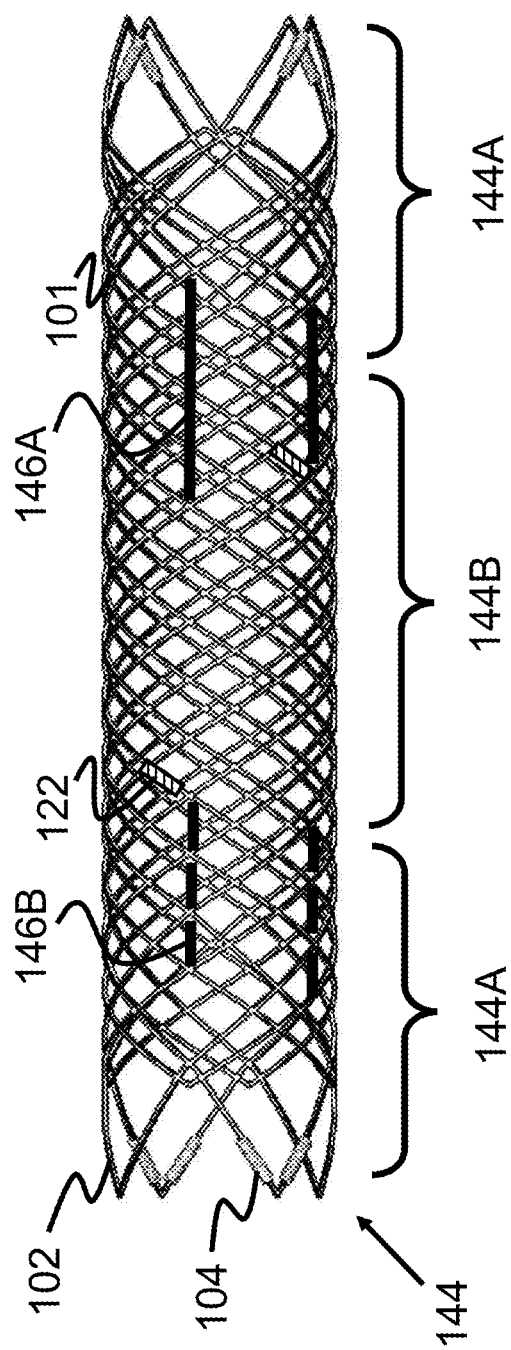
FIG. 5 illustrates a side view of a stent having regions of different longitudinal compression strength, according to one embodiment.
Figure 6:
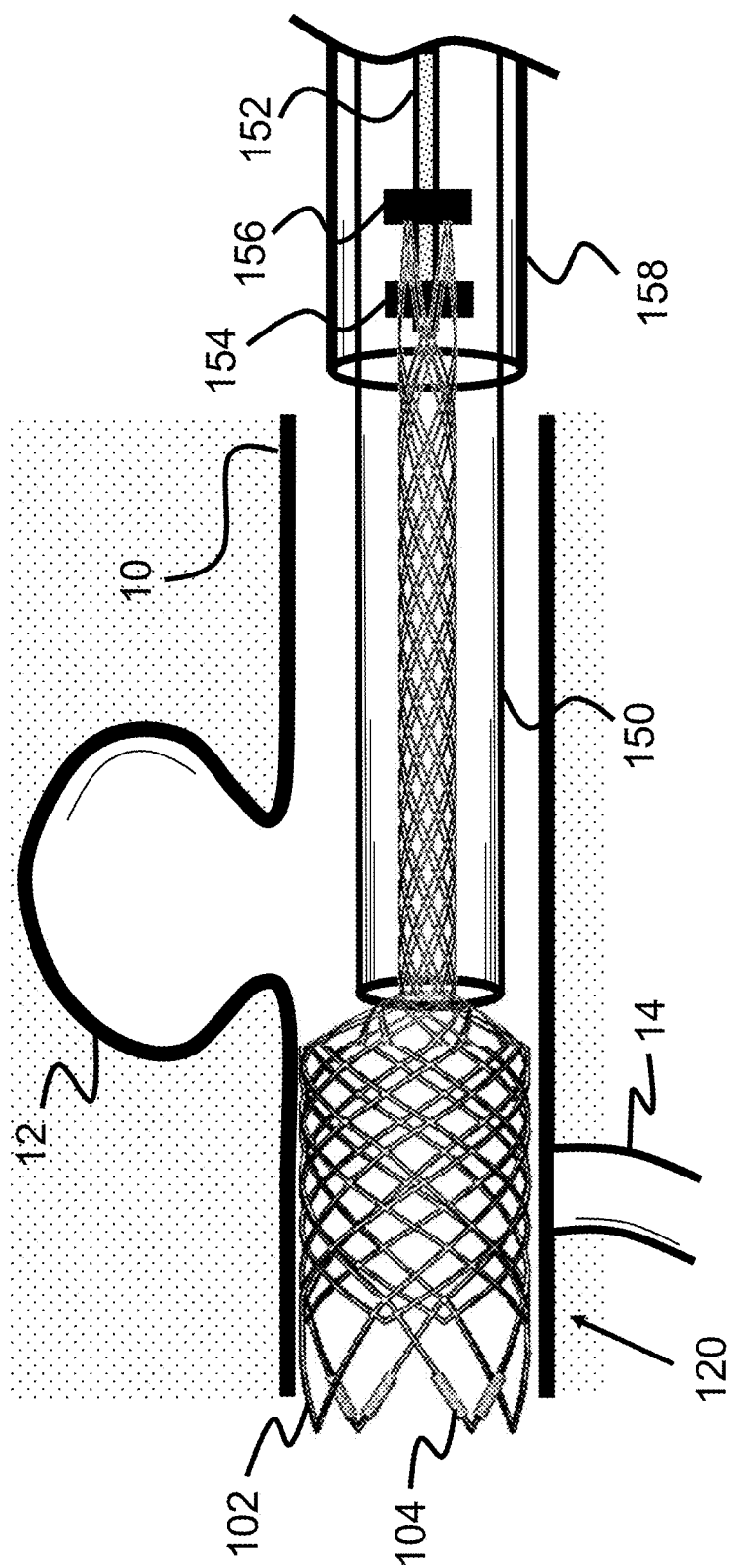
FIG. 6 illustrates a side view of a stent delivery method, according to one embodiment.
Figure 7:
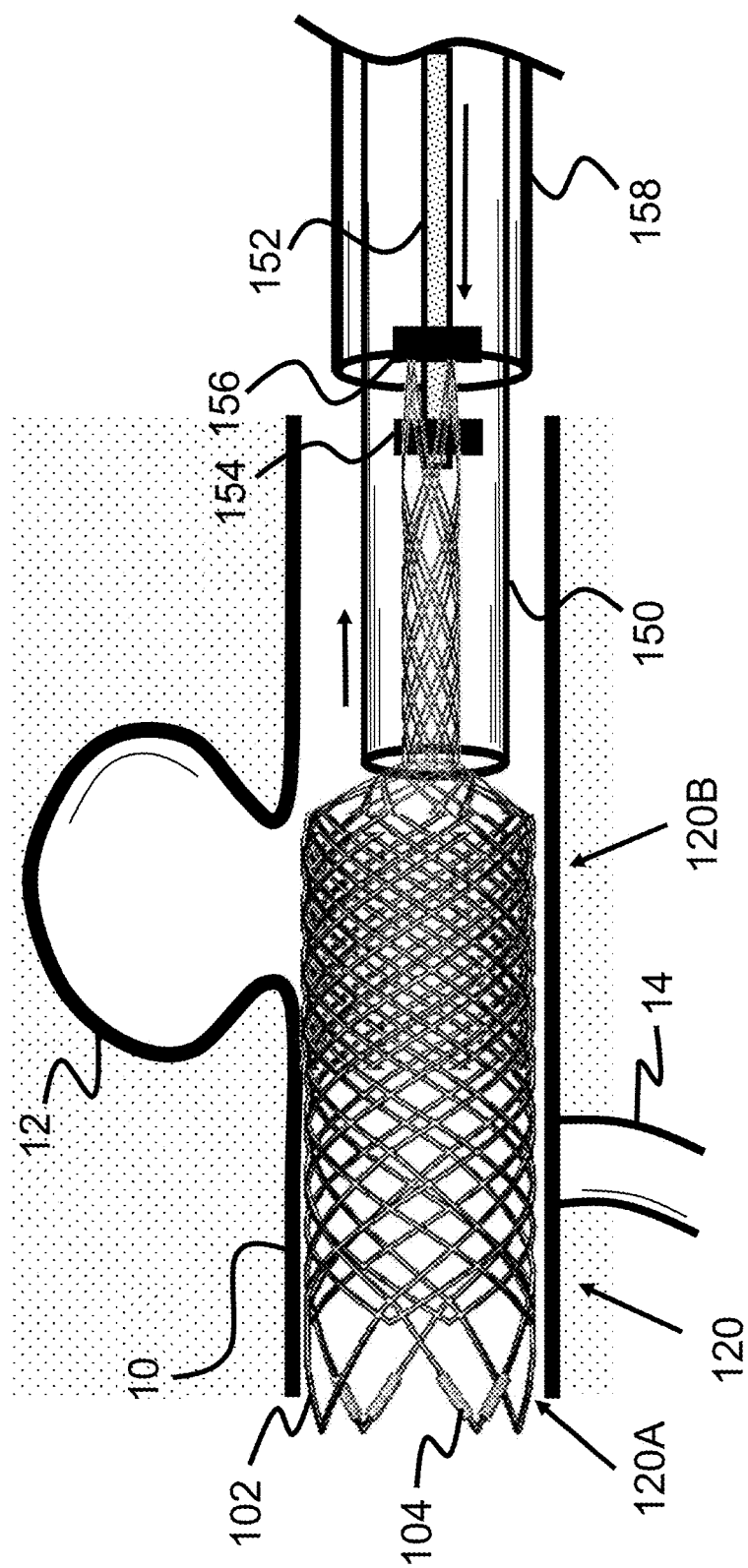
FIG. 7 illustrates a side view of a stent delivery method, according to one embodiment.

FIGS. 6 and 7 illustrate an example method of deploying a stent according to one embodiment. Typically, a guidewire (not shown) is advanced into a patient so that its distal end is positioned at or near a target site, such as an aneurysm. Next, a relatively larger guide catheter 158 is advanced over the guidewire so that its distal end is positioned at or near the delivery site, as seen in FIG. 5, and the guidewire is removed.

A delivery device is then advanced through the guide catheter. The delivery device can comprise a delivery catheter 150 having an elongated lumen, passage, or channel between its proximal and distal ends. The delivery device can also comprise an elongated pusher 152 that is longitudinally movable within the lumen, passage, or channel of the delivery catheter 150. The pusher preferably includes a mechanism on or near its distal end that can engage the stent 120 and allow the stent 120 to be distally pushed by the pusher 152. Please note, though this is illustratively shown with regard to stent 120, any variety of stent embodiments utilizing the various approaches described herein to achieve a stent with regions of differing porosity may be used.

For example, the pusher may include a distal raised protrusion 154 and a proximal raised protrusion 156. These protrusions can take the form of radiopaque cylinders, star shapes, or other similar shapes. The distal raised protrusion 154 is preferably sized to fit within openings of the stent 120, such as loops 102, while the proximal raised protrusion 156 is sized and positioned to abut a proximal end of the stent (e.g., the end of stent loop 102). Hence, the stent 120 can be distally pushed and retracted back into the microcatheter if needed. Again, a variety of different pushers and other stent engagement mechanisms can alternately be used, such as those seen in the patents previously incorporated by reference in this specification.

As seen in FIG. 6, the delivery catheter 150 is typically advanced to a location distally beyond the aneurysm 12 or at the distal end of the target site. The pusher 152 may be held in place while the delivery catheter 150 is proximally withdrawn to expose a distal end of the stent 120, which radially expands to engage and anchor to the vessel 10.

As seen in FIG. 7, the pusher 152 is advanced distally by the physician and the delivery catheter 150 is retracted proximally to cause the stent 120 to be longitudinally pushed forward to create a higher porosity middle region 120B relative to the original or lower porosity end region 120A. This pushing and pulling can be performed simultaneously or can be performed in small, alternating increments. The ratio or amount of the pushing and pulling generally will determine the porosity of the higher porosity region 120B, in addition to other known factors, such as wire size, braid pattern, stent diameter, etc.

Figure 8A:
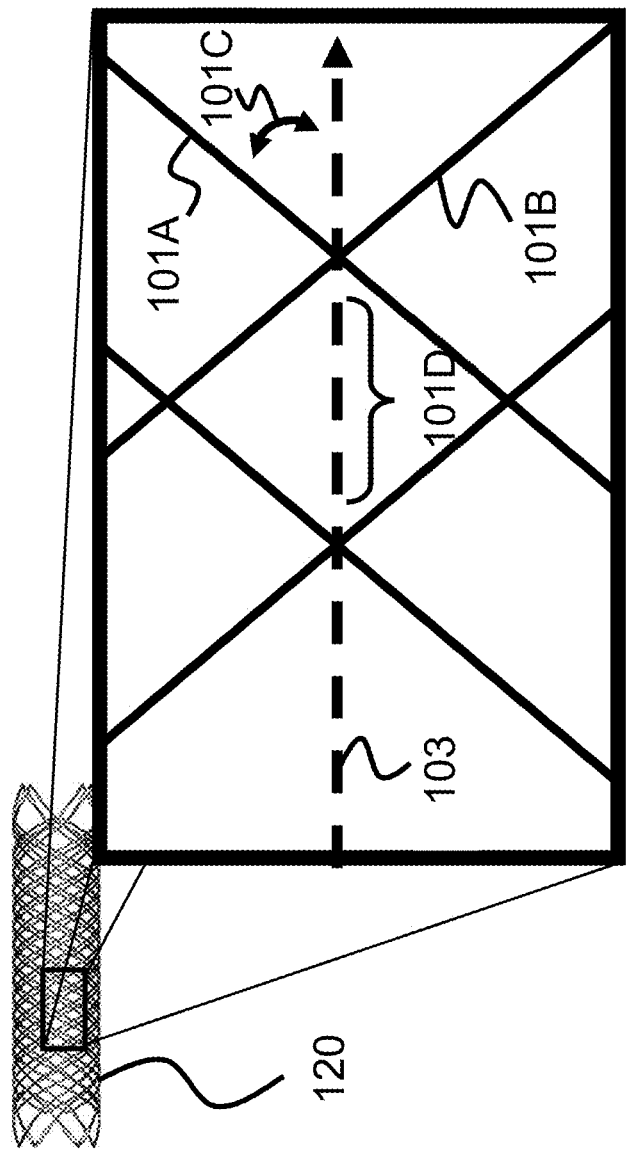
FIGS. 8A and 8B illustrate views of a changing braid angle, according to one embodiment.
Figure 8B:
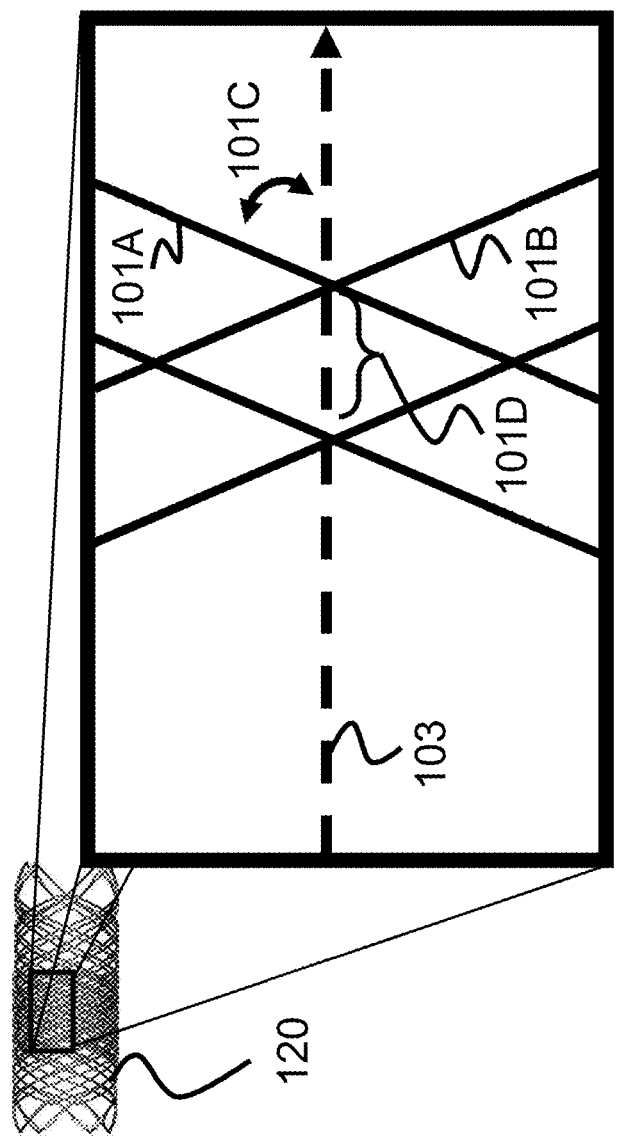

Braided stents typically demonstrate exponential increases in their metal coverage and reduction in porosity as the braiding angle (weave angle) increases. Hence, braided stents are often designed and engineered by adjusting the braid or weave angle based on the desired metal coverage and opening force. For example, FIG. 8A illustrates a magnified portion of stent 120 in which a first wire 101A crosses over at a second wire 101B to create a braid angle 101C between the longitudinal axis 103 of the stent 120 and one of the wires 101A. FIG. 8B illustrates that as a region of the stent 120 is longitudinally compressed, the braid angle 101C increases which results in a smaller length 101D of the pore/opening along a direction parallel to the stent axis 103 (e.g. diamond shape in the figures). Since these openings or diamonds become narrower along in a direction parallel to the axis of the stent (i.e., between left and right on the figures), the pick-per-inch increases, the percent metal coverage increases, and the porosity decreases in that longitudinally compressed region of the stent.

Figure 9:
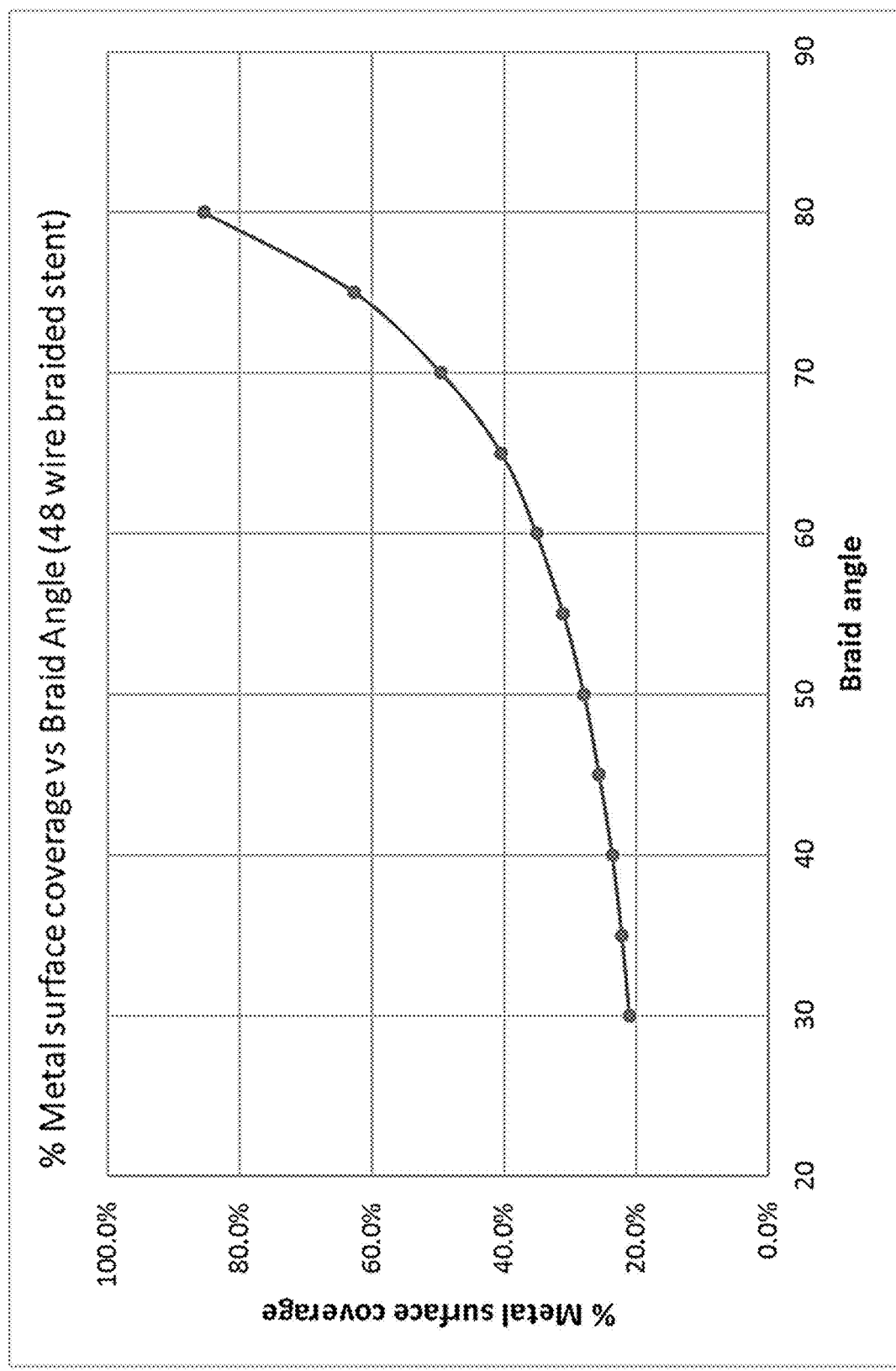
FIG. 9 illustrates a chart of the percent metal surface coverage to braid angle for an example stent, according to one embodiment.
Figure 10:
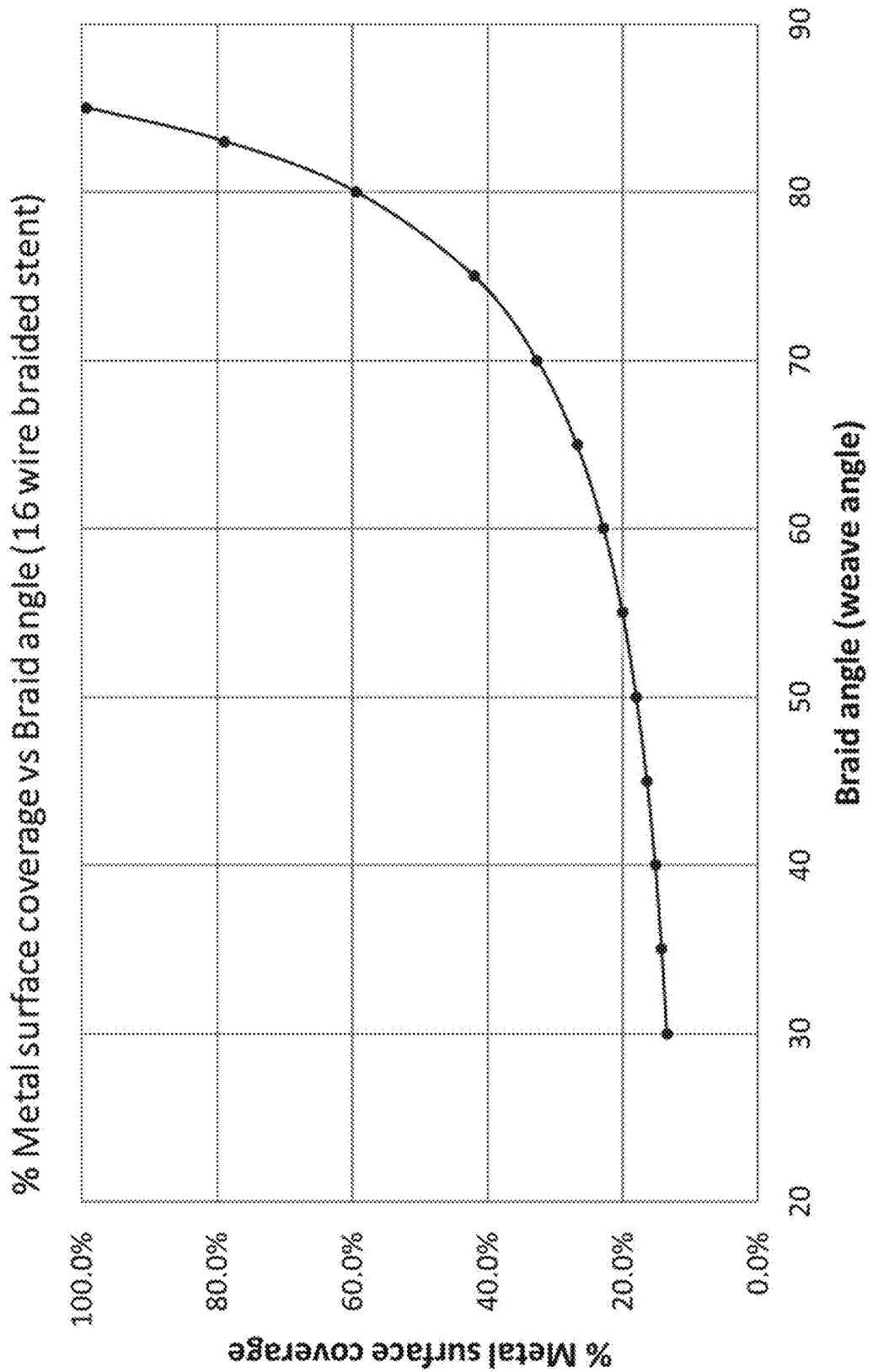
FIG. 10 illustrates a chart of the percent metal surface coverage to braid angle for an example stent, according to one embodiment.

FIG. 9 illustrates one example simulation graph that illustrates the changes in metal surface coverage as the braid angle changes for a 48 wire stent (representing a typical single layer flow diverter stent, given the relatively high wire count). FIG. 10 illustrates another example simulation graph that illustrates the changes in metal surface coverage as the braid angle changes for a 16 wire stent (representing a typical coil assist or intraluminal support stent, given the relatively low wire count). Based on the braid angle of each stent design, the percent metal coverage can be generally quantified. Note that while specific numbers of wires are mentioned, this wire "number" may refer to portions of wire located cross sectionally in the braid pattern of the stent. For example, a single wire can be braided back and forth between a proximal and distal end of the stent to produce the 16 or 48 "wires" or wire portions (or other wire numbers). Hence, the term "wires" in this context should not necessarily be taken literally to refer to separate wire pieces.

The percent metal surface coverage is the inverse of porosity, in that percent metal surface coverage plus percent porosity will theoretically total about 100%. Where porosity indicates the percent of open space in the stent, the percent metal surface coverage represents the percentage of the stent covered by the metallic stent elements. In this manner, a low percentage metal surface coverage corresponds to a high percentage porosity, and a high percentage metal surface coverage corresponds to a low percentage porosity. In this way, a higher braid angle corresponds to a higher percent metal surface coverage in turn corresponding to a lower porosity.

These example stents have a diameter of about 4 mm, constructed from 16 wires having a diameter of about 60 microns or 48 wires having a diameter of about 31.75 microns. Using mathematical principles of relation between braid angle, braid pitch, and the number of revolutions of the braid, different constructs and corresponding percentage metal surface areas can be obtained. For the two designs, the percent metal surface coverage rises exponentially once the braid angle crossed about 60 degrees. The rise is more stable between about 30 to 60 degrees. In one embodiment, a braided stent designed at braid angle of about 60 degrees characterizes metal coverage of about 35%. The metal coverage can be increased in the region of interest by controlled longitudinal compression (along long axis of the stent) from about 35% to 80%.

Figure 11:
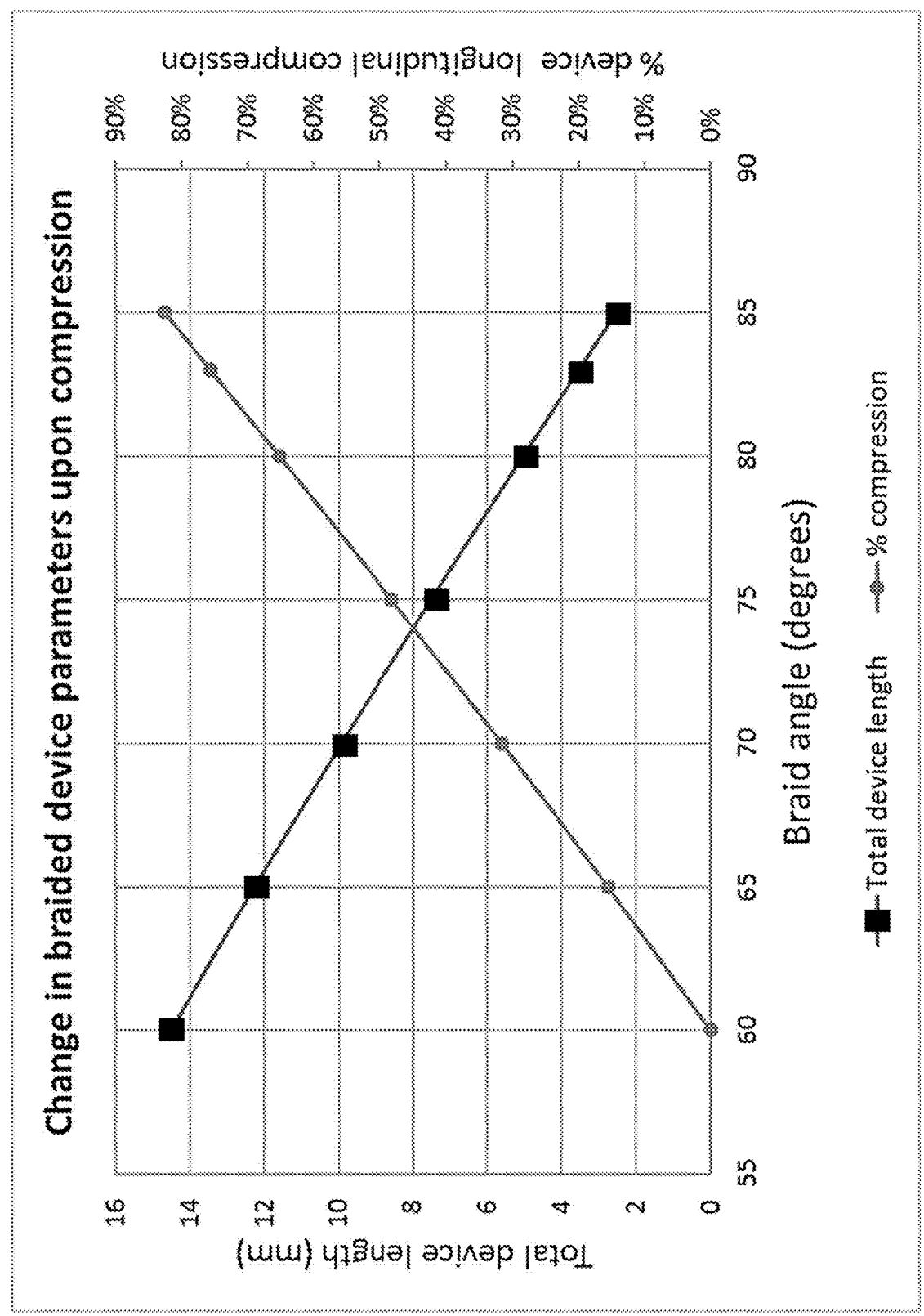
FIG. 11 illustrates a chart of the stent length to braid angle for an example stent, according to one embodiment.

FIG. 11 illustrates the interplay between longitudinal compression, change in device braid angle, and change in device length obtained by maintaining the overall wire length constant and varying the braid angle and pitch to simulate compression for a 16 wire braided stent (e.g., FIG. 10). A longitudinal compression of about 50% changes the braid angle from about 60 degrees to about 75 degrees and increases the metal coverage from 22% to 42%—nearly doubling the metal coverage.

Table 1 below illustrates several example amounts of pushing the pusher and pulling the delivery catheter to achieve a desired braid angle and therefore increase the porosity or percent coverage of a region of a stent (e.g., the example stent of FIG. 10). A typical prior art stent delivery will seek to provide no net pushing or longitudinal compression. For example, a delivery catheter may be mostly withdrawn from a pusher to expose the stent and allow it to radially expand. Alternately, a physician may push the pusher while retracting the outer delivery catheter to produce no net longitudinal compression on the stent, as seen in the first row of Table 1. Hence, in the prior art delivery technique, the initial braid angle of a portion of the delivered stent is the same as the final braid angle of the delivered stent, producing no percent increased coverage or porosity decrease.

TABLE 1

| Amount of Push (mm) | Amount of Pull (mm) | Initial braid angle | Final braid angle | % increase in metal coverage |
|---|---|---|---|---|
| 1 | 1 | 60 | 60 | None |
| 1.5 | 1 | 60 | 70 | 17.2 |
| 2.0 | 1 | 60 | 75 | 84.1 |
| 3.0 | 1 | 60 | 80 | 245 |

However, Table 1 also shows, according to at least one embodiment, that increased amounts of distal pushing on the pusher 152 relative to proximal pulling/withdrawal of the delivery catheter 150 results in a net amount of longitudinal compression that increases the final braid angle in regions of the stent, producing a percent increased coverage or porosity decrease. The net amount of longitudinal compression applied to the stent 120 will generally determine how much the final braid angle (e.g., FIG. 8B) changes relative to the initial braid angle (e.g., FIG. 8A) and therefore the percent increase in metal coverage of a region of the stent 120.

In one embodiment, a physician can perform the previously discussed pushing on the pusher 152 and pulling on the delivery catheter via hand by grasping each device. In one embodiment, the pusher 152, the delivery catheter 150, or both can include a plurality of measurement indicia that help indicate the position of the devices relative to each other and to the outer guide catheter 158.

Figure 12:
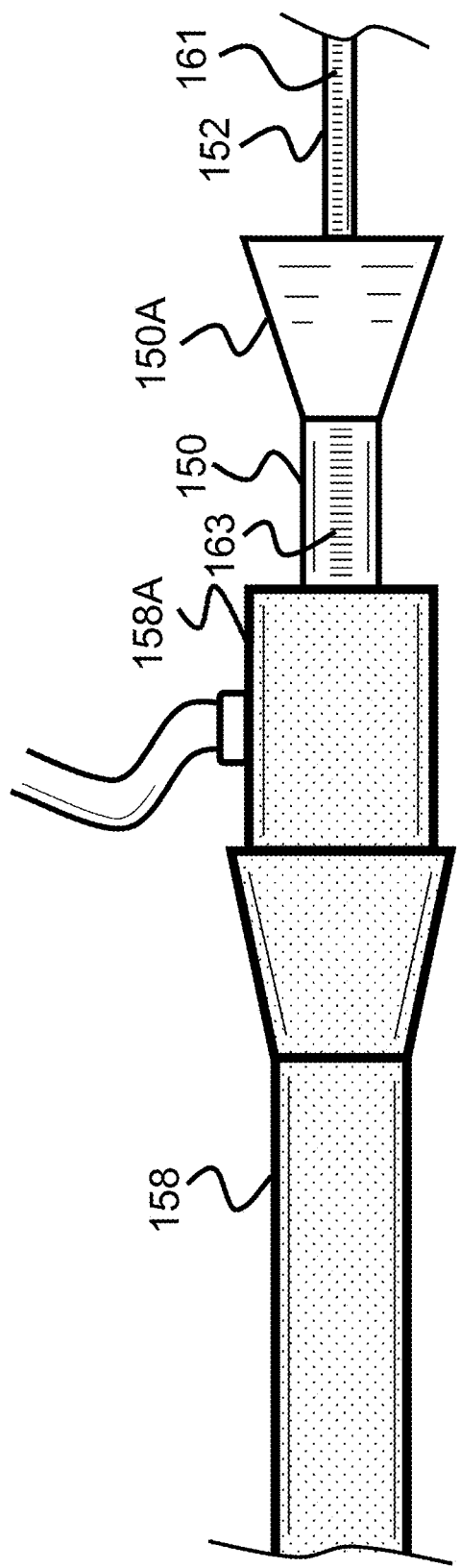
FIG. 12 illustrates a side view of delivery system, according to one embodiment.

For example, FIG. 12 illustrates proximal ends of the guide catheter 158, delivery catheter 150, and pusher 152. The pusher 152 may include a plurality of measurement indicia 161 along at least a proximal portion of its length to illustrate its movement relative to a proximal end of the delivery catheter 150 (e.g., delivery catheter hub 150A). Similarly, the delivery catheter 150 includes a plurality of measurement indicia 163 along at least a proximal portion of its length to illustrate its movement relative to the outer guide catheter 158 (e.g., guide catheter hemostatic valve 158A). Hence, a physician may better determine the push/pull amounts and ratio of the pusher 152 and delivery catheter 150.

Figure 13:
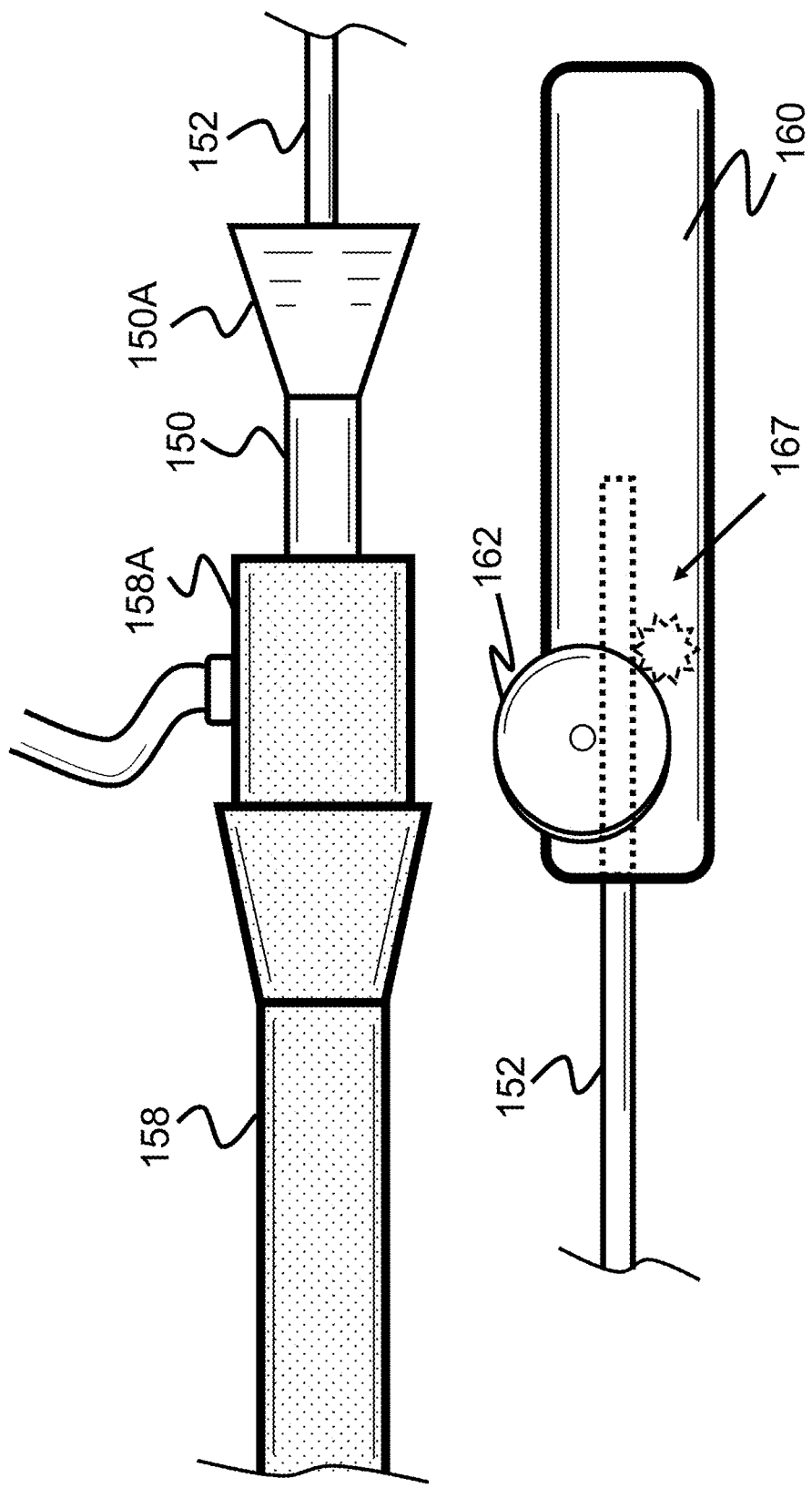
FIG. 13 illustrates a side view of delivery system, according to one embodiment.

FIG. 13 illustrates another embodiment which includes a handle 160 that connects to a proximal portion of the pusher 152 and thereby allows the user to more precisely distally advance the pusher 152 via a user interface element, such as a thumbwheel 162. For example, the thumbwheel 162 may be connected to a gear arrangement (e.g., rack and pinion 167) within the handle 160 that further connects to the pusher 152 (e.g., via a clamping mechanism). In one embodiment, the thumbwheel 160 can be configured to have a plurality of rotational detents that indicate movement of the pusher 152 a specific distance (e.g., 1 mm) so that the physician can better determine the amount of longitudinal compression and thereby the final porosity of a region of the stent 120. The previously described indicia may also be included to help further communicate relative movement of the pusher 152 and delivery catheter 150 to each other.

Figure 14:
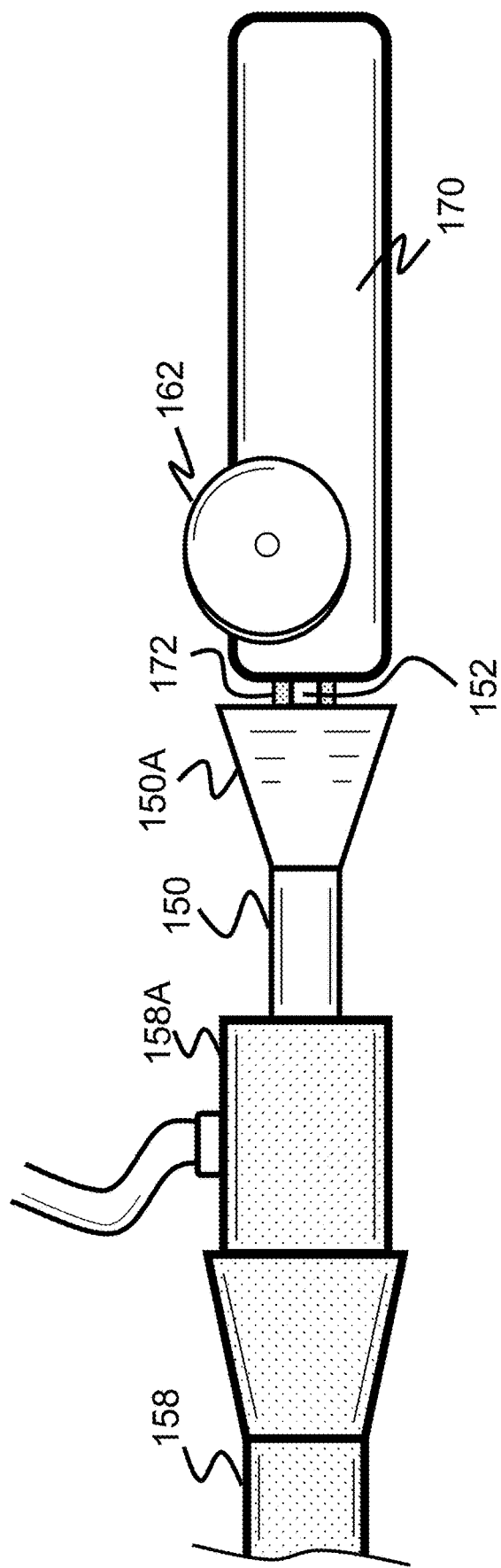
FIG. 14 illustrates a side view of delivery system, according to one embodiment

FIG. 14 illustrates an alternate embodiment of a handle 170 that not only is configured to move the pusher 152 but further connects to and moves the delivery catheter 150. In one example, the handle 170 may include a tube 172 that is positioned around the pusher 152 and that is connected to a proximal end of the delivery catheter (e.g., hub 150A). This arrangement allows the handle 170 to distally push the pusher 152 and proximally retract the delivery catheter 152.

In one embodiment, the thumbwheel 162 can control movement of both the pusher 152 and the delivery catheter 150 at the same time. Additionally, the gear mechanism within the handle 170 can be such that pushes and pulls in a predetermined ratio to achieve a predetermined porosity of a stent region (e.g., one of the ratios in Table 1). The handle 170 may further include a ratio adjustment member (e.g., switch, wheel, button, etc.) that changes the push/pull ratio. Hence, a physician can determine the desired porosity amount on the handle 170 during a procedure.

Figure 15:
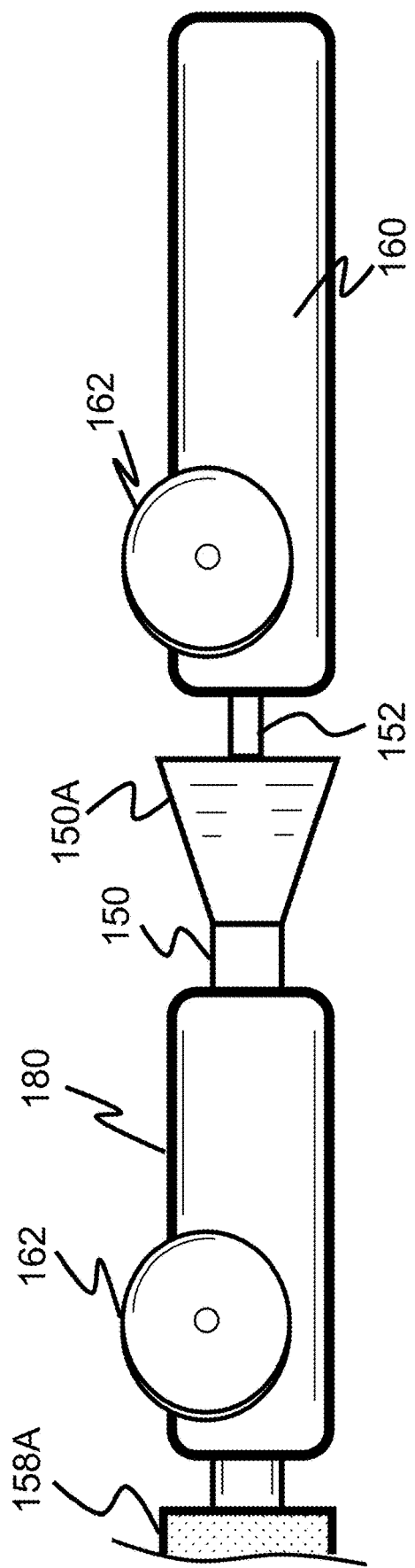
FIG. 15 illustrates a side view of delivery system, according to one embodiment.

FIG. 15 illustrates another embodiment in which a previously described handle 160 can be used to move the pusher 152 and a separate, but similar handle 180 can be used to move the delivery catheter 150. These handles 160 and 180 can be configured to produce one or more push/pull ratios between the pusher 152 and the delivery catheter 150, and can include an adjustment mechanism so that the user can adjust the push/pull ratio to a desired amount. Additionally, the previously described indicia can also be used to help monitor relative position changes between these devices.

Any of the previously described handles can be manually driven via a thumbwheel or similar mechanism, or by an electric motor. In that respect, the handles may further include an electronic interface that can monitor and display position changes and be electronically configured to adjust or produce a desired push/pull ratio. In one embodiment, an electronic interface can be included that allows a user to input characteristics of a stent such as manufacturer, model, braided wire numbers, expanded diameter size, etc., then input a desired porosity or percent coverage of a region of a stent, and then automatically determine the appropriate push/pull amounts of the pusher 152 and delivery catheter 150. The electronic interface can determine this push/pull ration by consulting a stored database or chart, or by performing calculations based on the inputted information.

The handle concepts can additionally have some benefits when used with a DFT stent (described earlier as utilizing one or more drawn-filled tube wires thereby rendering an entire stent visible without the need for additional radiopaque elements). One advantage is that a physician can use the handle to create a certain desired porosity or metal surface coverage area profile for at least a portion of the stent, and then visually determine if that configured profile is suitable for the particular procedure (e.g., if the stent appears to be configured to form its intended purpose—for instance, if a portion of the stent configured for flow diversion purposes is shaped to accomplish this task). If further refinement is necessary, the physician can then use the handle to further change the delivered shape of the stent.

Additionally, where no such handle concepts are utilized and instead the physician is using a push/pull technique (pushing the stent while retracting the catheter to change the porosity profile of a section of the stent), the use of a DFT stent will allow the physician to visually determine how the stent is responding to the use of the technique and then can adjust the technique (e.g., push the pusher more, or pull the catheter more) to adjust the desired porosity profile of the stent. In other words, the ability to view the stent as it changes its shape and porosity profile in real time has a tangible benefit as far as the physician determining how to adjust the stent during delivery.

Please note, though this is one particular advantage to a highly radiopaque stent such as DFT where an entirety or substantial entirety of a stent is visible due to the inclusion of DFT wire, this benefit is observed to some degree for other stents where at least a significant portion of the stent is visible. One advantage with a DFT stent though is that no additional radiopaque components have to be added to the stent for visualization, so the entirety of the stent itself is easily visualized using only the structural DFT wires forming the stent.

While the present embodiments have been described in terms of providing stents, systems, and delivery techniques to cause longitudinal compression to decrease a stent's porosity, it should be clear that an inverse procedure is also possible. Specifically, a physician may deploy a stent that is relatively less porous in its native state but can be increased in porosity in certain regions. For example, this can be achieved with similar stent regions of varying longitudinal compression and with techniques in which the pusher is proximally pulled relative to the delivery catheter.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A stent comprising:
one or more structural wires braided to form a tubular shape;
a first stent region of the tubular shape having a first longitudinal resistance to compression;
one or more longitudinal support wires located in the first stent region, the one or more longitudinal support wires being oriented parallel to a longitudinal axis extending through a center of the tubular shape;
a second stent region of the tubular shape having a second longitudinal resistance to compression that is lower than the first longitudinal resistance to compression; and,
wherein the first stent region and the second stent region are adjacent in the longitudinal direction.

2. The stent of claim 1, wherein the first stent region and the second stent region are initially deployable with a first porosity, and wherein the second stent region is longitudinally compressible during delivery relative to the first stent region to form a second porosity that is lower than the first porosity.

3. The stent of claim 1, wherein the one or more longitudinal support wires have a diameter larger than the one or more structural wires.

4. The stent of claim 1, wherein the one or more longitudinal support wires are composed of a material different than the one or more structural wires.

5. The stent of claim 1, wherein the one or more structural wires are composed of drawn filled tubes.

6. The stent of claim 1, wherein the one or more structural wires have a smaller diameter within the second stent region.

7. The stent of claim 1, wherein the one or more structural wires comprise a first braiding pattern in the first stent region and a second braiding pattern in the second stent region.

8. The stent of claim 1, further comprising a third stent region having said first longitudinal resistance to compression and being located adjacent to the second stent region and on an opposite side of the first stent region.

9. A stent comprising:
a tubular shape formed from one or more braided stent wires and comprising a first stent region and a second stent region adjacent to the first stent region;
the first stent region having a first longitudinal resistance to compression;
one or more support wires located in the first stent region, the one or more support wires being oriented parallel to a longitudinal axis extending through a center of the tubular shape;
the second stent region having a second longitudinal resistance to compression that is lower than the first longitudinal resistance to compression; and,
wherein the first stent region and the second stent region are adjacent in the longitudinal direction.

10. The stent of claim 9, further comprising a third stent region having the first longitudinal resistance to compression, wherein the third stent region is adjacent to the second stent region.

11. The stent of claim 9, wherein the one or more support wires are braided with the one or more braided stent wires; the one or more support wires having a larger diameter than the one or more braided stent wires.

12. The stent of claim 9, wherein the one or more support wires are connected to the stent by a plurality of ties.

13. The stent of claim 9, wherein the one or more support wires comprise a plurality of support wires that include linearly attached wires relative to the longitudinal axis of the stent.

14. The stent of claim 9, wherein the second stent region longitudinally compresses when a force of an inclusive range of 1-5 pounds is applied from a delivery device.

15. The stent of claim 9, wherein areas of the one or more braided stent wires comprising the first stent region further comprise a coating that increases longitudinal resistance to compression and wherein areas of the one or more braided stent wires comprising the second stent region are free of the coating.

16. A stent comprising:
a tubular shape formed from one or more braided stent wires and comprising a first stent region and a second stent region adjacent to the first stent region;
the first stent region having a first longitudinal resistance means to resist up to a first level of longitudinal compression force;
one or more support wires located in the first stent region, the one or more support wires being oriented parallel to a longitudinal axis extending through a center of the tubular shape;
the second stent region having a second longitudinal resistance means to resist up to a second level of longitudinal compression that is lower than the first level of longitudinal compression; and,
wherein the first stent region and the second stent region are adjacent in the longitudinal direction.

17. The stent of claim 1, wherein the one or more longitudinal support wires are slidably connected to the one or more structural wires.

18. The stent of claim 1, wherein each of the one or more longitudinal support wires is comprised of a plurality of wire segments.

19. The stent of claim 9, wherein the one or more support wires are connected to the one or more braided stent wires by a plurality of loosely configured ties such that each end of the one or more support wires may slide along a length of the stent.

20. The stent of claim 16, wherein the one or more support wires are slidably connected to the first stent region.

* * * * *